(12) United States Patent
Waga et al.

(10) Patent No.: US 8,776,597 B2
(45) Date of Patent: Jul. 15, 2014

(54) CAPACITIVE TYPE HUMIDITY SENSOR AND MANUFACTURING METHOD THEREOF

(75) Inventors: Satoshi Waga, Niigata-ken (JP);
Sumihito Morita, Niigata-ken (JP);
Masaru Sakurai, Niigata-ken (JP);
Masaya Yamatani, Niigata-ken (JP);
Hideki Kamimura, Niigata-ken (JP)

(73) Assignee: Alps Electric Co., Ltd., Tokyo (JP)

( * ) Notice: Subject to any disclaimer, the term of this patent is extended or adjusted under 35 U.S.C. 154(b) by 533 days.

(21) Appl. No.: 13/232,589

(22) Filed: Sep. 14, 2011

(65) Prior Publication Data

US 2012/0000285 A1 Jan. 5, 2012

Related U.S. Application Data

(63) Continuation of application No. PCT/JP2010/055027, filed on Mar. 24, 2010.

(30) Foreign Application Priority Data

Mar. 31, 2009 (JP) ................................ 2009-086591

(51) Int. Cl.
*G01N 27/22* (2006.01)
*B81B 7/00* (2006.01)
(52) U.S. Cl.
CPC ............ *G01N 27/223* (2013.01); *G01N 27/225* (2013.01); *B81B 7/0032* (2013.01)
USPC ...................................................... 73/335.04
(58) Field of Classification Search
CPC .. B81B 7/0032; B81B 7/0045; B81B 7/0048; B81B 7/0051; B81B 7/0054; B81B 7/0058; B81B 7/0064; B81B 7/0007; B81B 7/0077; B81B 2207/115; G01N 27/223; G01N 27/225; G01N 27/226; G01N 27/227; G01N 27/22
See application file for complete search history.

(56) References Cited

U.S. PATENT DOCUMENTS 4,838,089 A * 6/1989 Okada et al. .................... 73/727
5,396,795 A * 3/1995 Araki ......................... 73/204.26
(Continued)

FOREIGN PATENT DOCUMENTS

| JP | 2004-093470 | 3/2004 |
| JP | 2004-093474 | 3/2004 |

(Continued)

OTHER PUBLICATIONS

PCT/JP2010/055027, English Translation of Interntional Preliminary Report on Patentability Chapter I, Mar. 31, 2009.*

(Continued)

*Primary Examiner* — Lisa Caputo
*Assistant Examiner* — Puman Roy
(74) *Attorney, Agent, or Firm* — Brinks Gilson & Lione

(57) ABSTRACT

A capacitive type humidity sensor is provided, where a sensor chip substrate, with a sensor section where electrostatic capacitance changes in accordance with humidity, a reference section where electrostatic capacitance does not change, and a plurality of pads which are output terminals of each section, and an IC substrate, which is electrically connected to the pads and which outputs the difference in capacitance between the sections as a voltage, are fixed to the same support substrate, where a protective member, which forms a sealed region surrounding the sensor section and which covers the reference section, is provided on the sensor chip substrate, the support substrate is covered by a sealing resin except for the region which is covered by the protective member, the sensor section is exposed to air at the region which is surrounded by the protective member, and the other constituent elements are covered by the sealing resin.

7 Claims, 9 Drawing Sheets

(56) References Cited

U.S. PATENT DOCUMENTS

| | | | |
|---|---|---|---|
| 5,948,991 A * | 9/1999 | Nomura et al. | 73/727 |
| 5,952,588 A * | 9/1999 | Young | 73/862.626 |
| 6,307,258 B1 * | 10/2001 | Crane et al. | 257/680 |
| 6,483,324 B1 * | 11/2002 | Mitter et al. | 324/689 |
| 6,528,723 B2 | 3/2003 | Fries et al. | 174/551 |
| 6,534,711 B1 * | 3/2003 | Pollack | 174/529 |
| 6,540,963 B2 * | 4/2003 | Sugiyama | 422/98 |
| 6,962,282 B2 * | 11/2005 | Manansala | 228/180.5 |
| 7,243,561 B2 * | 7/2007 | Ishigami et al. | 73/866.1 |
| 7,644,615 B2 * | 1/2010 | Arisaka | 73/335.04 |
| 7,901,971 B2 * | 3/2011 | Hunziker et al. | 438/55 |
| 7,989,938 B2 * | 8/2011 | Okada et al. | 257/680 |
| 7,994,618 B2 * | 8/2011 | Dehe et al. | 257/684 |
| 8,148,808 B2 * | 4/2012 | Braden et al. | 257/687 |
| 8,222,707 B2 * | 7/2012 | Ou | 257/433 |
| 8,640,538 B2 * | 2/2014 | Kono et al. | 73/204.26 |
| 2002/0136664 A1 | 9/2002 | Lee et al. | |
| 2004/0061222 A1 * | 4/2004 | Bai | 257/734 |
| 2006/0001116 A1 * | 1/2006 | Auburger et al. | 257/433 |
| 2006/0037393 A1 | 2/2006 | Itakura et al. | |
| 2006/0037404 A1 * | 2/2006 | Watanabe | 73/714 |
| 2006/0238290 A1 | 10/2006 | Arisaka | |
| 2007/0126130 A1 * | 6/2007 | Dehe et al. | 257/787 |
| 2008/0148842 A1 * | 6/2008 | Oda | 73/204.26 |
| 2009/0072333 A1 * | 3/2009 | Haag et al. | 257/415 |
| 2014/0077314 A1 * | 3/2014 | Humbert et al. | 257/414 |
| 2014/0077824 A1 * | 3/2014 | Niimi et al. | 324/664 |

FOREIGN PATENT DOCUMENTS

| | | | |
|---|---|---|---|
| JP | 2006300835 A * | 11/2006 | |
| JP | 2006-337110 | 12/2006 | |
| JP | 2007-127612 | 5/2007 | |
| JP | 2007248065 A * | 9/2007 | |
| JP | 2008064561 A * | 3/2008 | |
| JP | 2008107166 A * | 5/2008 | |
| WO | 2004/023126 A1 | 3/2004 | |

OTHER PUBLICATIONS

PCT/JP2010/055027, English Translation of the Written Opinion of the International Search Authority, Mar. 31, 2009.*

* cited by examiner

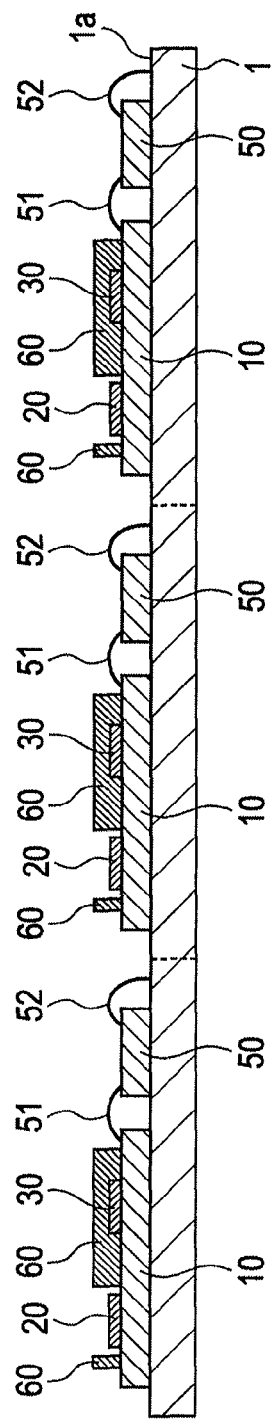
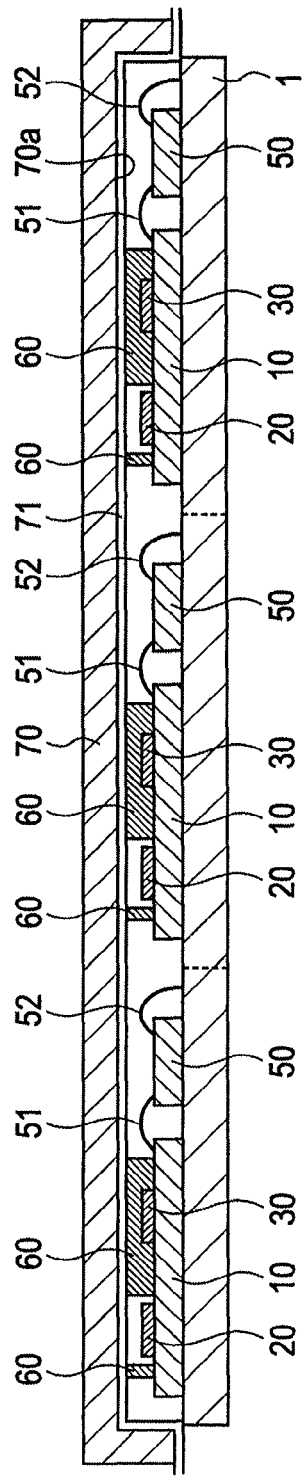

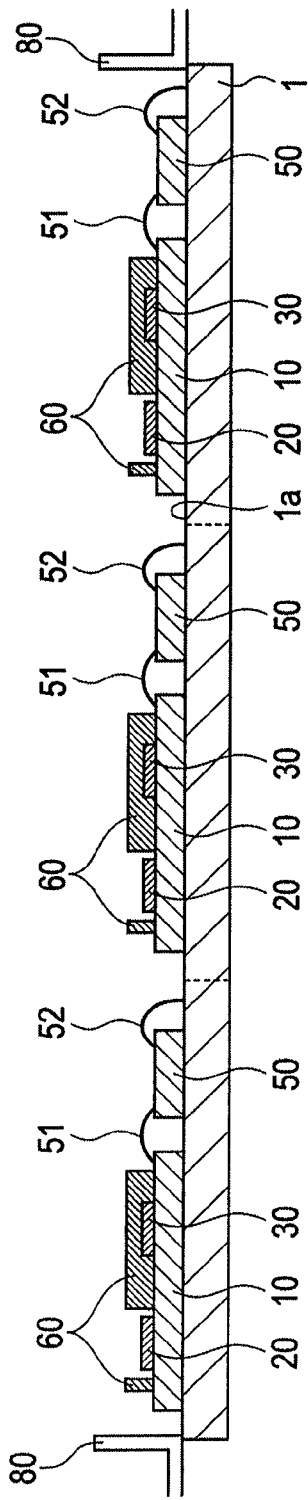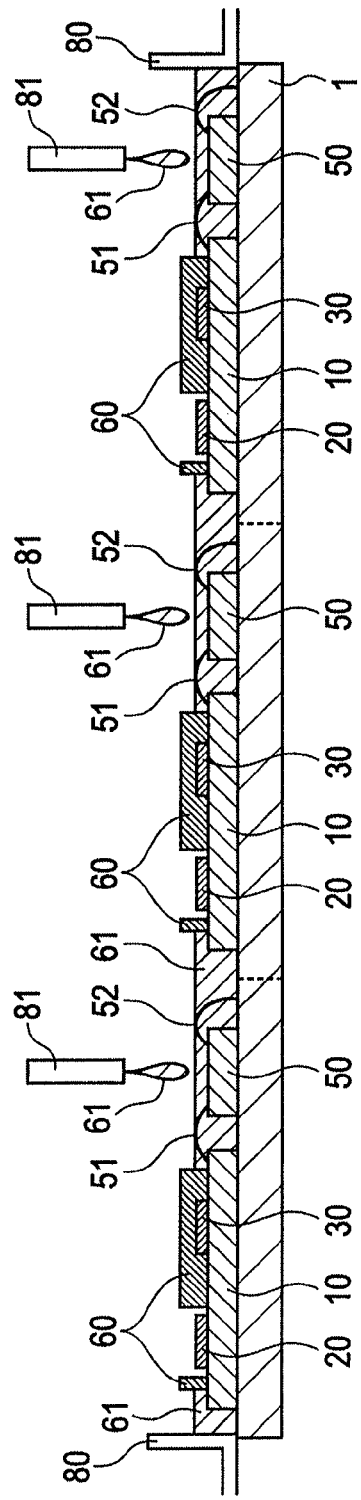

CAPACITIVE TYPE HUMIDITY SENSOR AND MANUFACTURING METHOD THEREOF

CLAIM OF PRIORITY

This application is a Continuation of International Application No. PCT/JP2010/055027 filed on Mar. 24, 2010, which claims benefit of Japanese Patent Application No. 2009-086591 filed on Mar. 31, 2009. The entire contents of each application noted above are hereby incorporated by reference.

BACKGROUND

1. Field of the Disclosure

The present disclosure relates to a capacitive type humidity sensor with a humidity-sensitive polymer film as dielectrics and a manufacturing method thereof.

2. Description of the Related Art

Humidity sensors, which uses a measurement of humidity change, include an electrostatic capacitive type humidity sensor with a humidity-sensitive polymer film, where a permitivity changes in accordance with the amount of moisture which is absorbed or released, as dielectrics. The capacitive type humidity sensor is provided with the humidity-sensitive polymer film and a sensor section formed of a pair of electrodes which are covered with the humidity-sensitive polymer film and which detect electrostatic capacitance, and it is possible for pads which are provided at an edge portion of the pair of electrodes to be electrically connected to an external circuit using wire bonding. A capacitive type humidity sensor such as this is, for example, disclosed in Japanese Unexamined Patent Application Publication No. 2008-107166.

In the structure in the related art described above, there is a problem in that the humidity-sensitive polymer film and the bonding wire become exposed and the bonding wire is susceptible to impact and corrosion. In particular, in a structure where a control IC which is an external circuit is provided on the same support substrate as the sensor section, there is a desire to seal the entire substrate so as to protect the control IC and the wire bonding section from damage due to impact and corrosion, but it is necessary that the humidity-sensitive polymer film of the sensor section is exposed to air and it is not possible to perform a sufficient seal.

In addition, among the capacitive type humidity sensors, there is a type where a sensor section where the electrostatic capacitance changes in accordance with humidity and a reference section which maintains a constant electrostatic capacitance irrespective of humidity are provided on the same substrate and the difference in capacitance between the sensor section and the reference section is converted into a voltage and output the voltage. In this type, there is a concern that, if the substrate surface is exposed and the humidity-sensitive polymer film of the sensor portion is exposed to air, it may not be possible to obtain sufficient sealing of the reference portion.

SUMMARY

A capacitive type humidity sensor includes a sensor chip substrate, which has a sensor section and a reference section, and an IC substrate are mounted on the same support substrate and a manufacturing method thereof, capable of preventing damage due to impact and corrosion of wire bonding and an IC substrate, and further, improving the sealing of the reference section.

A protective member is provided to cover from an outer periphery of the sensor section to the reference section. Thus, it is possible to secure a space where the sensor section is exposed to air at an inner side of the protective member, to improve the sealing of the reference section using the protective member, and to seal the constituent elements other than the sensor section at an outer side of the protective member using a resin material.

That is, according to an aspect of the invention, there is provided a capacitive type humidity sensor where a sensor chip substrate, which is provided with a sensor section where electrostatic capacitance changes in accordance with humidity, a reference section where electrostatic capacitance does not change depending on humidity, and a plurality of pads which are output terminals of the sensor section and the reference section, and an IC substrate, which is electrically connected to the plurality of pads via a conductive wire and which converts the difference in capacitance between the sensor section and the reference section into a voltage and outputs the voltage, are adhered and fixed to the same support substrate, where a protective member, which forms a sealed region surrounding the sensor section and which covers the reference section, is provided on the sensor chip substrate, the support substrate is covered by a sealing resin except for the region which is covered by the protective member, the sensor section is exposed to air at the region which is surrounded by the protective member, and the pads, the conductive wire, and the IC substrate are covered by the sealing resin. In practice, the surface height of the sealing resin and the surface height of the protective member match.

In addition, according to another aspect of the invention, there is provided a manufacturing method of a capacitive type humidity sensor including a step of preparing a plurality of sensor chip substrates which are provided with a sensor section where electrostatic capacitance changes in accordance with humidity, a reference section where electrostatic capacitance does not change depending on humidity, and a plurality of pads which are output terminals of the sensor section and the reference section, and forming a protective member, which forms a sealed region surrounding the sensor section and covers the reference section, on the sensor chip substrate; a step of preparing a plurality of IC substrates which convert the difference in capacitance between the sensor section and the reference section into a voltage and output the voltage; a step of preparing a single supporting substrate which has a plurality of sensor areas which are partitioned using a dicing line; a step of adhering and fixing the sensor chip substrates, which are formed with the protective member, and the IC substrates as pairs in each of the sensor areas on the upper surface of the support substrate; a step of electrically connecting the pads of the sensor chip substrate and the IC substrate using a conductive wire; a step of preparing a mold which has a concave portion which regulates a cavity for resin injection and fixing the mold to the upper surface of the supporting substrate in a state where the concave portion of the mold and the upper surface of the protective member provided on the sensor chip substrate are in contact with each other; a step of injecting a sealing resin which has been melted into the cavity formed between the concave surface of the mold and the upper surface of the support substrate at an outer side of the protective member and hardening the sealing resin; a step of removing the mold; and a step of cutting out the support substrate along the dicing line. The mold is preferably fixed to the supporting substrate in a state where the concave portion of the mold is adhered to a release sheet.

BRIEF DESCRIPTION OF THE DRAWINGS

FIG. 4 is a cross-sectional diagram illustrating one step of the manufacturing process of a capacitive type humidity sensor according to a first embodiment of the invention;

FIG. 5 is a cross-sectional diagram illustrating the next step of FIG. 4;

FIG. 10 is a cross-sectional diagram illustrating the next step of FIG. 9;

FIG. 11 is a cross-sectional diagram illustrating the next step of FIG. 10;

DESCRIPTION OF THE EXEMPLARY EMBODIMENTS

Figure 1:
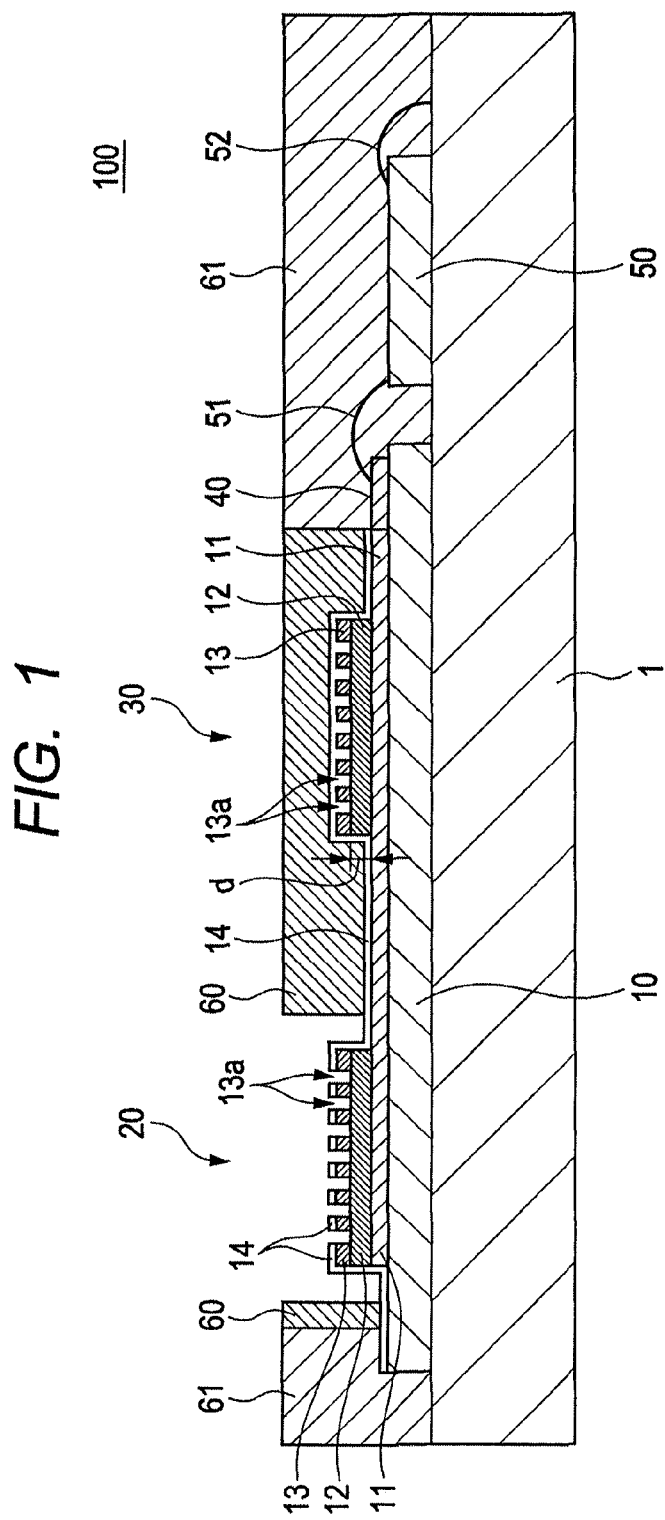
FIG. 1 is a cross-sectional diagram illustrating the main configuration of a capacitive type humidity sensor according to an embodiment of the present invention (a cross sectional diagram along a line I-I of FIG. 2)
Figure 2:
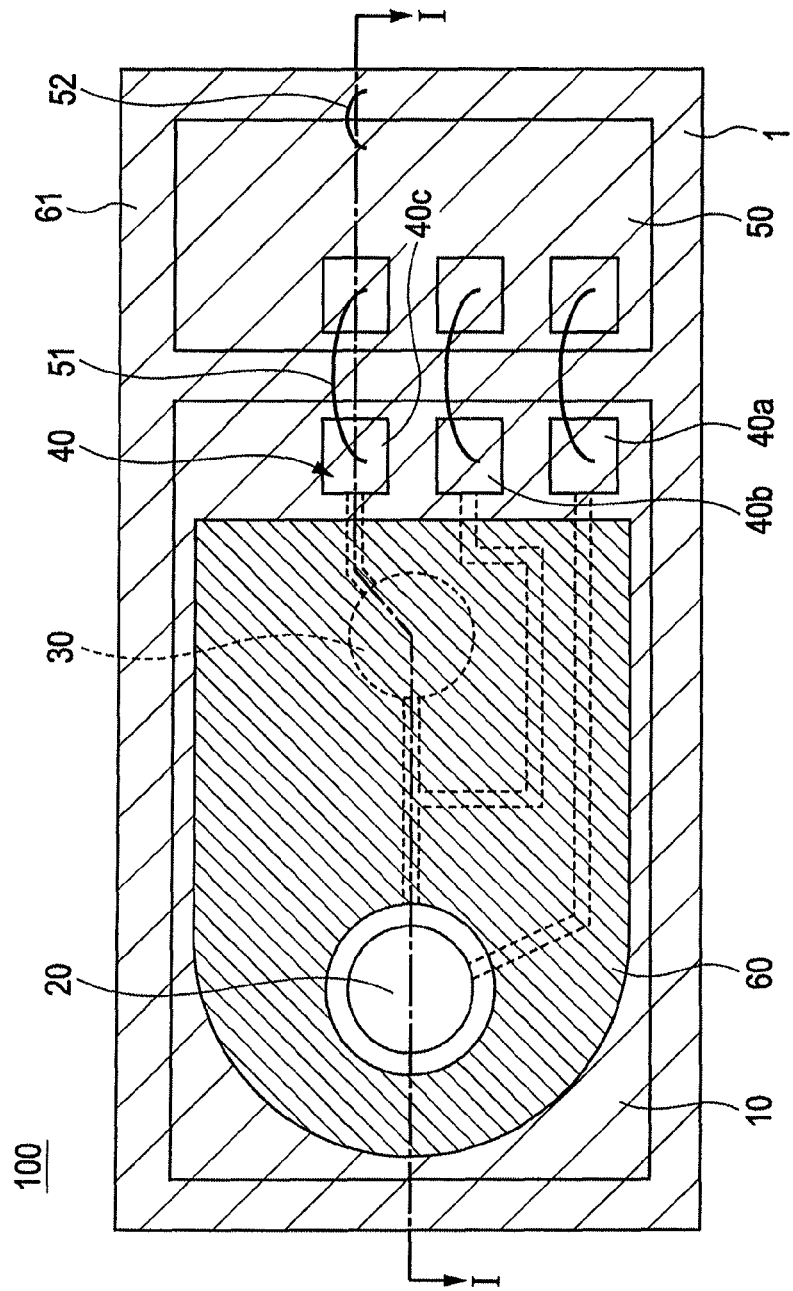
FIG. 2 is a planar diagram illustrating the capacitive type humidity sensor.

FIGS. 1 and 2 are respectively a cross-sectional diagram and a planar diagram which show the main configuration of a capacitive type humidity sensor 100 according to an embodiment of the invention. The capacitive type humidity sensor 100 is a polymer film humidity sensor with a humidity-sensitive polymer material, where a permittivity changes in accordance with the amount of moisture which is absorbed or released, as dielectrics. The capacitive type humidity sensor 100 has a sensor chip substrate 10 and an IC substrate 50 which are adhered and fixed on a single support substrate 1.

In the sensor chip substrate 10 which is formed from, for example, silicon, a sensor section 20, where an electrostatic capacitance C20 changes in accordance with humidity, a reference section 30, where a constant electrostatic capacitance C30 is maintained irrespective of humidity, and a plurality of pads 40, which are output terminals of the sensor section 20 and the reference section 30, are formed.

Figure 3:
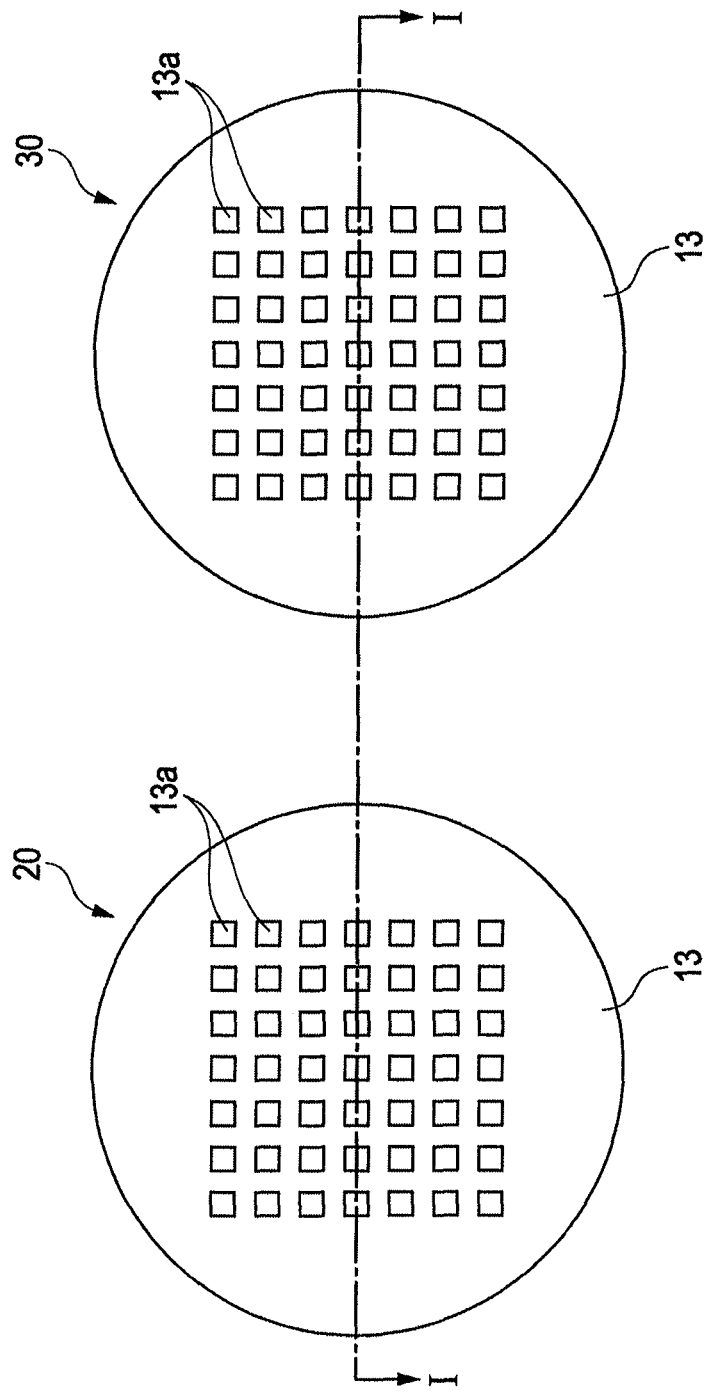
FIG. 3 is a planar diagram illustrating a parallel plate structure which is common to a sensor section and a reference section of the capacitive type humidity sensor.

The sensor section 20 and the reference section 30 have the same parallel plate structure which is formed from a lower electrode film 11, a humidity-sensitive polymer film 12, and an upper electrode film 13 formed by the same process using the same materials. The parallel plate structure is shown in FIG. 3. The lower electrode film 11, the humidity-sensitive polymer film 12, and the upper electrode film 13 are formed by being laminated on the sensor chip substrate 10 in order from the lower electrode film 11 and have substantially the same circular shape in a planar view. The lower electrode film 11 and the upper electrode film 13 are, for example, formed from an electrode material such as Al and the thickness of each is uniform. The humidity-sensitive polymer film 12 is formed from a polyimide and is formed with the same thickness. A distance d between the lower electrode film 11 and the upper electrode film 13 is the same as the thickness of the humidity-sensitive polymer film 12, and an electrostatic capacitance C which accumulates between the lower electrode film 11 and the upper electrode film 13 is determined by the permitivity $\epsilon$ of the humidity-sensitive polymer film 12, the distance d between the lower electrode film 11 and the upper electrode film 13, and an opposing area S ($C=\epsilon S/d$).

In the upper electrode film 13, a plurality of openings 13$a$ which expose the humidity-sensitive polymer film 12 are provided. The plurality of openings 13$a$ are opened up and lined up at predetermined intervals in the left, right, up, and down directions in a region which faces the lower electrode film 11 and form a planar rectangular shape. The number, the planar shape, and the formation position of the openings 13$a$ are arbitrary. The cross section along a line I-I of FIG. 3 is shown in FIG. 1.

In the reference section 30, a non-moisture-permeating protective film 14 which stops the transfer of moisture with air is formed over the upper electrode film 13, and the openings 13$a$ of the upper electrode film 13 are covered by the non-moisture-permeating protective film 14. The non-moisture-permeating protective film 14 is, for example, a silicon nitride film (SiNx film) or a laminate film of $Al_2O_3$ and $SiO_3$. Since the humidity-sensitive polymer film 12 is covered by the upper electrode film 13 and the non-moisture-permeating protective film 14 and is not exposed to air, the amount of moisture in the humidity-sensitive polymer film 12 does not change even if the humidity (moisture) in the air changes and the permitivity $\epsilon$ also does not change. According to this, the constant electrostatic capacitance (reference capacitance) C30 is maintained between the lower electrode film 11 and the upper electrode film 13.

On the other hand, in the sensor section 20, the non-moisture-permeating protective film 14 covers only the upper electrode film 13 and the plurality of openings 13$a$ provided in the upper electrode film 13 are not covered by the non-moisture-permeating protective film 14. Since the humidity-sensitive polymer film 12 is exposed to the air via the plurality of openings 13$a$, the amount of moisture, which is absorbed or released in accordance with humidity (amount of moisture) in the air, changes and the permitivity $\epsilon$ changes. As a result, the electrostatic capacitance (sensor capacitance) C20 between the lower electrode film 11 and the upper electrode film 13 changes.

The plurality of pads 40 is formed from a pad 40$a$ which is provided at an end portion of a wire conductor which extends from the upper electrode film 13 on the sensor section 20, a pad 40$b$ which is provided at an end portion of a wire conductor which branches out from the wire conductor connected to the lower electrode films 11 of each of the sensor section 20 and the reference section 30, and a pad 40$c$ which is provided at an end portion of a wire conductor which extends from the upper electrode film 13 on the reference section 30. The plurality of pads is not covered by the non-moisture-permeating protective film 14.

In the IC substrate 50 which is formed from, for example, silicon, a control circuit (control IC) is formed which is electrically connected to the sensor section 20 and the reference section 30 of the sensor chip substrate 10 via the plurality of pads 40 and which converts the difference $\Delta C$ ($=C20-C30$) between the sensor section 20 and the reference section 30 into a voltage and outputs the voltage. The pad of the control circuit and the plurality of pads 40 of the sensor chip substrate 10 are electrically connected by a conductive wire 51. In addition, the IC substrate 50 is grounded to the support substrate 1 by the conductive wire 52 (FIG. 1).

The capacitive type humidity sensor 100 which has the entire configuration described above is provided with a protective member 60, which forms a sealed region surrounding the sensor section 20 and completely covers the outer periphery of the sensor section 20 and the reference section 30 on the sensor chip substrate 10, and the support substrate 1 is sealed by sealing resin 61 at an outer side of the protective member 60. The sealing resin 61 completely covers the pads 40 on the sensor chip substrate 10, the entire IC substrate 50, and the conductive wires 51 and 52. The surface height of the sealing resin 61 matches with the surface height of the protective member 60. In the sealing resin 61, an epoxy resin which includes, for example, a $SiO_2$ filler is used, and in the protective member 60, either of, for example, a resin material, silicon, or glass is used. The protective member 60 according to the embodiment is formed in a disc shape which has a larger diameter at its inner circumference surface than the diameter of the sensor section 20 which has a planar circular shape.

By providing the protective member 60, it is possible to secure a space where the sensor section 20 is exposed to air in the sealed region surrounded by the protective member 60, and the exposing of the sensor section 20 and the sealing of the constituent sections other than the sensor section 20 are compatible. Then, since the reference section 30 is covered by the protective member 60, due to the sealing resin 61, the reference section 30 does not receive damage and the sealing of the reference section 30 is improved. Furthermore, by using the sealing resin 61, it is possible to prevent corrosion and damage due to impact of the pads 40 of the sensor chip substrate 10, the IC substrate 50, and the conductive wires 51 and 52.

Next, a first embodiment of a manufacturing method of the capacitive type humidity sensor according to the invention will be described with reference to FIGS. 4 to 8. FIGS. 4 to 8 are cross-sectional diagrams which show the manufacturing process according to the first embodiment of the invention. In FIGS. 4 to 8, a detailed structure of the sensor section 20 and the reference section 30 and the pads 40 are omitted from the diagrams.

First, a plurality of sensor chip substrates 10 are prepared which are provided with the sensor section 20 where electrostatic capacitance changes in accordance with humidity, a reference section 30 where a constant electrostatic capacitance is maintained irrespective of humidity, and the pads 40 which are output terminals of the sensor section 20 and the reference section 30, and the protective member 60, which covers the outer periphery of the sensor section 20 and from the outer periphery of the sensor section 20 to the reference section 30, is formed on each of the sensor chip substrates 10. The protective member 60 is formed by either, for example, a resin material, silicon, or glass. In addition, a plurality of IC substrates 50 (FIGS. 1 and 2) are prepared where control circuits (control ICs) are formed so that the capacitance difference ΔC of the sensor capacitance C20 and the reference capacitance C30 is converted and output as a voltage. The number of the sensor chip substrates 10 and the IC substrates 50 which are prepared are the same.

Next, as shown in FIG. 4, the plurality of sensor chip substrates 10 and the IC substrates 50 are adhered and fixed to an upper surface 1a of the single support substrate 1. Dicing lines are provided in the left, right, down, and up directions in the support substrate 1, and the sensor chip substrates 10 and the IC substrates 50 are provided in pairs in each of a plurality of sensor areas which are partitioned by the dicing lines. For example, a resin sealant is used in the substrate fixing.

Next, as shown in FIG. 4, in each of the sensor areas, the pads 40 of the sensor chip substrate 10 and the pads of the IC substrate 50 are connected by the conductive wire 51, and the IC substrate 50 and the support substrate 1 are connected by the conductive wire 52.

Figure 6:
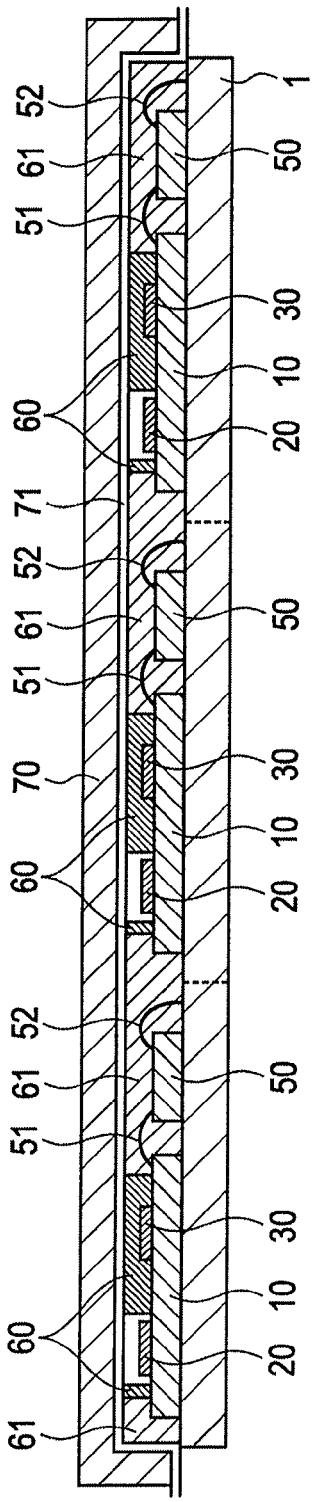
FIG. 6 is a cross-sectional diagram illustrating the next step of FIG. 5.
Figure 7:
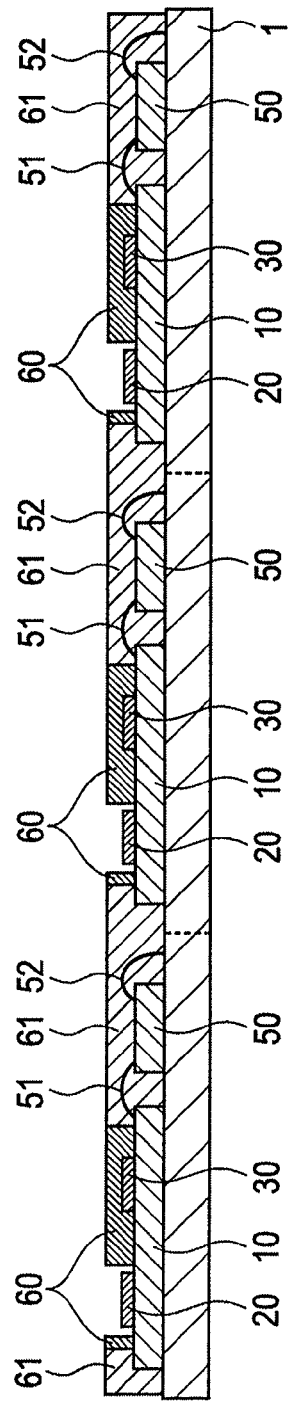
FIG. 7 is a cross-sectional diagram illustrating the next step of FIG. 6.

Next, as shown in FIGS. 5 to 7, the support substrate 1 is sealed using a transfer molding method. A mold 70, which has a concave portion 70a where a cavity is formed which stipulates the resin injection region, and a release sheet 71, which makes it easier to release the mold 70, are used in the sealing process.

More specifically, as shown in FIG. 5, the release sheet 71 is adhered to the concave portion 70a of the mold 70 and the mold 70 is fixed to the support substrate 1 with the release sheet 71 facing the upper surface 1a of the support substrate 1. In this fixed state, the upper surface of the protective member 60 provided on the sensor chip substrate 10 comes into contact with the concave portion 70a of the mold 70 through the release sheet 71, a sealed region (inner periphery side) which is surrounded by the protective member 60 is sealed by the mold 70, and a cavity is formed between the mold 70 and the support substrate 1 at the outer side of the region (outer periphery side) which is covered by the protective member 60. When the mold 70 is fixed in this manner, the sealing resin 61 which has been melted is injected into the cavity which is formed between the mold 70 and the support substrate 1 at the outer side of the protective member 60 as shown in FIG. 6. The sealing resin 61 which is injected fills in the outer side of the protective member 60, seals the IC substrate 50, the conductive wires 51 and 52, and the pads 40 of the sensor chip substrate 10, and does not enter the region surrounded by the protective member 60. Then, when the sealing resin 61 has hardened, the mold 70 is removed. The mold 70 is easily removed since the release sheet 71 is imposed between the sealing resin 61 and the mold 70. FIG. 7 shows the state after the mold 70 is removed. The surface height of the sealing resin 61 matches the surface height of the protective member 60.

Figure 8:
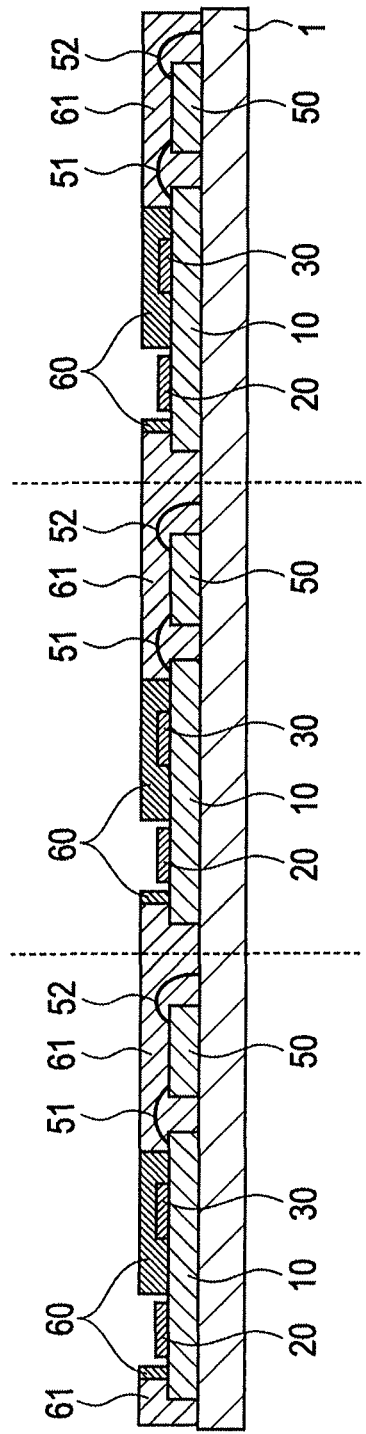
FIG. 8 is a cross-sectional diagram illustrating the next step of FIG. 7.

When the mold 70 is removed, the support substrate 1 is cut out along the dicing line as shown in FIG. 8 and individual capacitive type humidity sensors 100 (FIG. 1) are obtained.

Next, a second embodiment of a manufacturing method of the capacitive type humidity sensor according to the invention will be described with reference to FIGS. 9 to 14. FIGS. 9 to 14 are cross-sectional diagrams illustrating the manufacturing process according to the second embodiment of the invention. In FIGS. 9 to 14, a detailed structure of the sensor section 20 and the reference section 30 and the pads 40 are omitted from the diagrams.

First, a plurality of sensor chip substrates 10 are prepared which are provided with the sensor section 20 where electrostatic capacitance changes in accordance with humidity, a reference section 30 where a constant electrostatic capacitance is maintained irrespective of humidity, and the pads 40 which are output terminals of the sensor section 20 and the reference section 30, and the protective member 60, which covers the outer periphery of the sensor section 20 and from the outer periphery of the sensor section 20 to the reference section 30, is formed on each of the sensor chip substrates 10. The protective member 60 is formed by either, for example, a resin material, silicon, or glass. In addition, a plurality of IC substrates 50 (FIGS. 1 and 2) are prepared where control circuits (control ICs) are formed so that the capacitance difference ΔC of the sensor capacitance C20 and the reference capacitance C30 is converted and output as a voltage. The number of the sensor chip substrates 10 and the IC substrates 50 which are prepared are the same.

Figure 9:
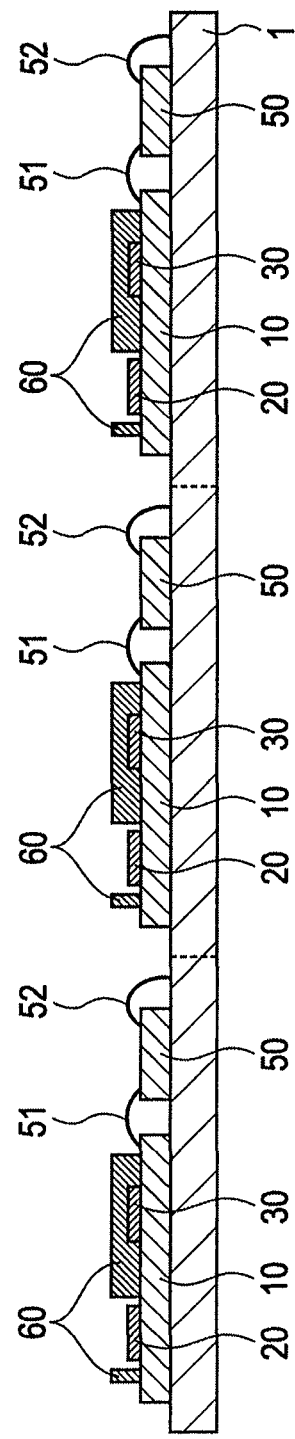
FIG. 9 is a cross-sectional diagram illustrating one step of the manufacturing process of a capacitive type humidity sensor according to a second embodiment of the invention.

Next, as shown in FIG. 9, the plurality of sensor chip substrates 10 and the IC substrates 50 are adhered and fixed to an upper surface 1a of the single support substrate 1. Dicing lines are provided in the left, right, down, and up directions in the support substrate 1, and the sensor chip substrates 10 and the IC substrates 50 are provided in pairs in each of a plurality of sensor areas which are partitioned by the dicing lines. For example, a resin sealant is used in the substrate fixing.

Next, as shown in FIG. 9, in each of the sensor areas, the pads 40 of the sensor chip substrate 10 and the pads of the IC substrate 50 are connected by the conductive wire 51, and the IC substrate 50 and the support substrate 1 are connected by the conductive wire 52. The steps until here are the same as the first embodiment described above.

Figure 12:
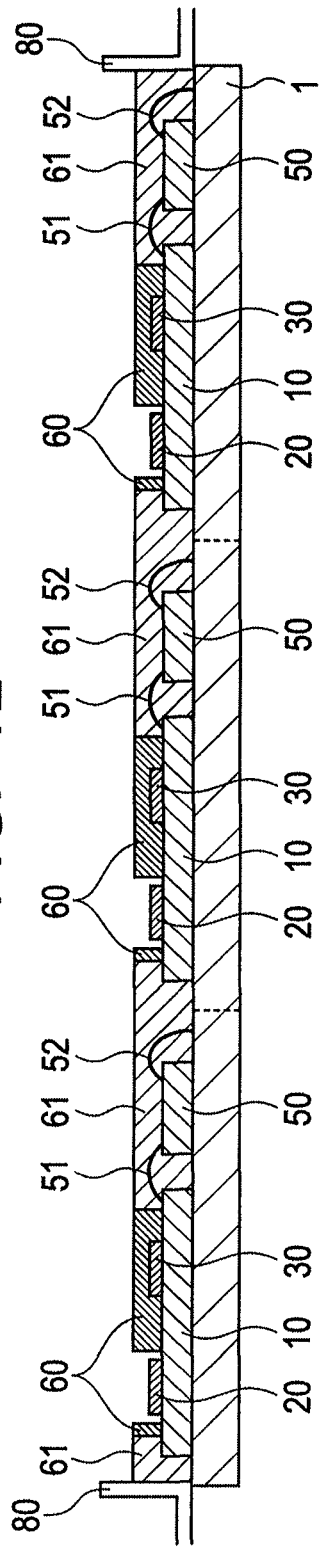
FIG. 12 is a cross-sectional diagram illustrating the next step of FIG. 11.
Figure 13:
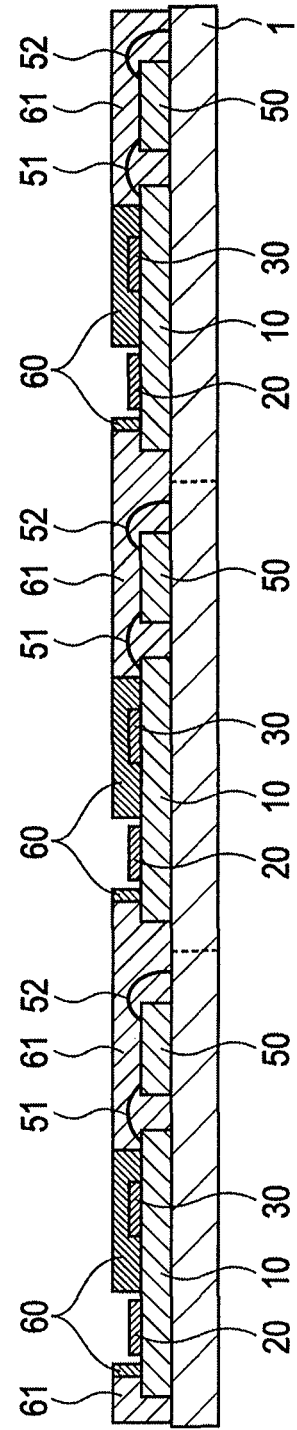
FIG. 13 is a cross-sectional diagram illustrating the next step of FIG. 12.

After the wire bonding, as shown in FIG. 10, an outer frame 80 is provided which regulates a cavity for a resin injection region in a periphery edge portion of the upper surface 1a of the support substrate 1. Then, as shown in FIGS. 11 and 12, the sealing resin 61 which has been melted is injected in the outer frame 80 on the outer side of the region covered by the protective member 60 using a resin dispenser 81. The injection of the sealing resin 61 is performed until the surface height matches the upper surface of the protective member 60. When the sealing resin 61 has hardened, the outer frame 80 is removed. FIG. 13 shows the state after the outer frame 80 is removed.

Figure 14:
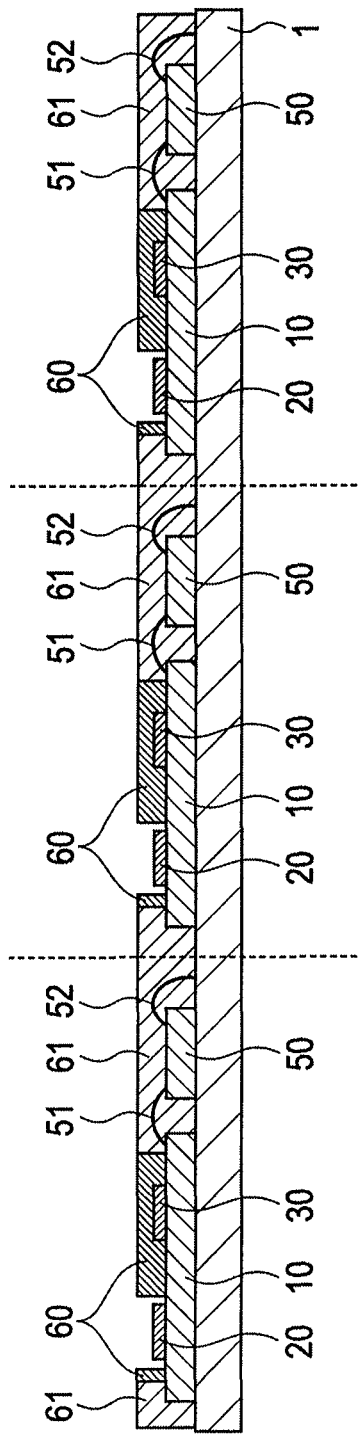
FIG. 14 is a cross-sectional diagram illustrating the next step of FIG. 13.

When the outer frame 80 is removed, the support substrate 1 is cut out along the dicing line as shown in FIG. 14 and individual capacitive type humidity sensors 100 (FIG. 1) are obtained.

According to the manufacturing methods of the first and the second embodiments, by providing the protective member 60 which covers the reference section 30 excluding the sealed region which surrounds the sensor section 20, it is possible to secure a space where the sensor section 20 is exposed to air and it is possible to perform resin molding all together on the support substrate 1 (excluding the space) and the constituent elements which are provided on the support substrate 1 other than the sensor section 20 and the reference section 30. According to this, the manufacturing process is easy and also a reduction in costs is achieved. In addition, since the reference section 30 is covered by the protective member 60 and not the sealing resin 61, in a case where a resin material with a filler mixed in is used as the sealing resin 61, it is possible to improve the sealing of the reference section 30 without the reference section 30 being damaged.

Above, the embodiments are described where the sensor section 20 and the reference section 30, which are formed from a parallel plate structure where the humidity-sensitive polymer film 12 is interposed between the lower electrode film 11 and the upper electrode film 13, are provided. However, it is possible to apply the invention also to a capacitive type humidity sensor with a structure where a sensor section and a reference section have a humidity-sensitive polymer film and a pair of electrodes which are covered by the humidity-sensitive polymer film and detect electrostatic capacitance thereof.

It should be understood by those skilled in the art that various modifications, combinations, sub-combinations and alterations may occur depending on design requirements and other factors insofar as they are within the scope of the appended claims of the equivalents thereof.

It is possible for the invention to be applied to a humidity sensor measuring the environment.

What is claimed is:

1. A capacitive type humidity sensor, comprising:
    a sensor chip substrate provided with a sensor section where electrostatic capacitance changes in accordance with humidity, a reference section where electrostatic capacitance does not change depending on humidity, and a plurality of pads which are output terminals of the sensor section and the reference section, and an IC substrate, which is electrically connected to the plurality of pads via a conductive wire and which converts the difference in capacitance between the sensor section and the reference section into a voltage and outputs the voltage, are adhered and fixed to the same support substrate,
    a protective member, which forms a sealed region surrounding the sensor section and covers the reference section, provided on the sensor chip substrate, the support substrate being covered by a sealing resin except for the region which is covered by the protective member, the sensor section being exposed to air at the region which is surrounded by the protective member, and the pads, the conductive wire, and the IC substrate are covered by the sealing resin.

2. The capacitive type humidity sensor according to claim 1,
    wherein the surface height of the sealing resin and the surface height of the protective member match.

3. The capacitive type humidity sensor according to claim 1,
    wherein the protective member comprises one of a resin material, silicon, or glass.

4. A manufacturing method of a capacitive type humidity sensor comprising:
    preparing a plurality of sensor chip substrates which are provided with a sensor section where electrostatic capacitance changes in accordance with humidity, a reference section where electrostatic capacitance does not change depending on humidity, and a plurality of pads which are output terminals of the sensor section and the reference section, and forming a protective member, which forms a sealed region surrounding the sensor section and covers the reference section, on the sensor chip substrate;
    preparing a plurality of IC substrates which convert the difference in capacitance between the sensor section and the reference section into a voltage and output the voltage;
    preparing a single supporting substrate which has a plurality of sensor areas which are partitioned using a dicing line;
    adhering and fixing the sensor chip substrates, which are formed with the protective member, and the IC substrates as pairs in each of the sensor areas on the upper surface of the support substrate;
    electrically connecting the pads of the sensor chip substrate and the IC substrate using a conductive wire;
    preparing a mold which has a concave portion which regulates a cavity for resin injection and fixing the mold to the upper surface of the supporting substrate in a state where the concave portion of the mold and the upper surface of the protective member provided on the sensor chip substrate are in contact with each other;
    injecting a sealing resin which has been melted into the cavity formed between the concave surface of the mold and the upper surface of the support substrate at an outer side of the protective member and hardening the sealing resin;
    removing the mold; and
    cutting out the support substrate along the dicing line.

5. The manufacturing method of a capacitive type humidity sensor according to claim 4, wherein the mold is fixed to the supporting substrate in a state where the concave portion of the mold is adhered to a release sheet.

6. A manufacturing method of a capacitive type humidity sensor comprising:

preparing a plurality of sensor chip substrates which are provided with a sensor section where electrostatic capacitance changes in accordance with humidity, a reference section where electrostatic capacitance does not change depending on humidity, and a plurality of pads which are output terminals of the sensor section and the reference section, and forming a protective member, which forms a sealed region surrounding the sensor section and covers the reference section, on the sensor chip substrate;

preparing a plurality of IC substrates which convert the difference in capacitance between the sensor section and the reference section into a voltage and output the voltage;

preparing a single supporting substrate which has a plurality of sensor areas which are partitioned using a dicing line;

adhering and fixing the sensor chip substrates, which are formed with the protective member, and the IC substrates as pairs in each of the sensor areas on the upper surface of the support substrate;

electrically connecting the pads of the sensor chip substrate and the IC substrate using a conductive wire;

a step of providing an outer frame which regulates a cavity for resin injection at an outer edge portion of the upper surface of the supporting substrate;

injecting a sealing resin which has been melted in the outer frame until the surface height matches the upper surface of the protective member at an outer side of the protective member and hardening the sealing resin;

removing the outer frame; and cutting out the support substrate along the dicing line.

7. The manufacturing method of a capacitive type humidity sensor according to claim 4, wherein the protective member comprises one of a resin material, silicon, or glass.

* * * * *